United States Patent
McSherry (10) Patent No.: US 8,961,896 B2
(45) Date of Patent: Feb. 24, 2015

(54) CYTOLOGICAL CELL SAMPLE COLLECTION, STORAGE, AND TRANSPORT DEVICE

(75) Inventor: Kathy Mary McSherry, San Diego, CA (US)

(73) Assignee: In HindSight LLC, San Diego, CA (US)

( * ) Notice: Subject to any disclaimer, the term of this patent is extended or adjusted under 35 U.S.C. 154(b) by 466 days.

(21) Appl. No.: 13/301,055

(22) Filed: Nov. 21, 2011

(65) Prior Publication Data

US 2014/0073988 A1   Mar. 13, 2014
US 2014/0378866 A9   Dec. 25, 2014

Related U.S. Application Data

(60) Provisional application No. 61/458,407, filed on Nov. 24, 2010.

(51) Int. Cl.
| | |
|---|---|
| *A61B 10/00* | (2006.01) |
| *C12M 1/00* | (2006.01) |
| *C12M 1/26* | (2006.01) |
| *C12M 3/00* | (2006.01) |
| *G01N 21/75* | (2006.01) |
| *G01N 31/22* | (2006.01) |

(Continued)

(52) U.S. Cl.
CPC .......... *A61B 10/02* (2013.01); *A61B 2010/0216* (2013.01)
USPC ...................... 422/411; 435/307.1; 435/309.1; 600/572

(58) Field of Classification Search
CPC ............... A61B 10/02; A61B 2010/02; A61B 2010/0216; A61M 2210/1067; A61M 2210/1078; A61M 2210/1089; A61M 2210/1092; A61M 2210/1096; A61M 2210/1475

USPC ........... 600/572; 435/2, 287.1, 29, 30, 287.4, 435/287.6, 309, 309.1, 307.1; 215/349, 215/344, 354; 128/205.13; 220/521, 522; 525/380, 379, 382; 436/165; 422/411; 156/60

See application file for complete search history.

(56) References Cited

U.S. PATENT DOCUMENTS 5,129,402 A  *  7/1992  Koll et al. ................... 600/572
5,477,863 A     12/1995  Grant (Continued)

FOREIGN PATENT DOCUMENTS

WO       99-38996 A1      8/1999
WO    2007009414 A1      1/2007

(Continued)

OTHER PUBLICATIONS

International Search Report and the Written Opinion for International App No. PCT/US2012/064164, completed Mar. 18, 2013, Korean Intellectual Property Office.

*Primary Examiner* — Brian Szmal
(74) *Attorney, Agent, or Firm* — Sheppard Mullin Richter & Hampton LLP (57) ABSTRACT

A cytological cell sample collection, storage, and transport device is disclosed. The device comprises a sheath, a collection assembly, a base, and a containment vial. The collection assembly is slidably coupled to the base to expose a swab head comprising the collection assembly. The containment vial is configured to enclose the sheath and collection assembly within the internal volume defined by the containment vial and the base.

20 Claims, 5 Drawing Sheets

(51) Int. Cl.
 *G01N 33/52* (2006.01)
 *A61B 10/02* (2006.01)

(56) References Cited

U.S. PATENT DOCUMENTS

| | | | |
|---|---|---|---|
| 7,993,871 B2* | 8/2011 | Skiffington et al. | 435/30 |
| 8,334,134 B2* | 12/2012 | Young et al. | 435/309.1 |
| 2002/0120074 A1* | 8/2002 | Wada et al. | 525/380 |
| 2003/0042220 A1* | 3/2003 | Bourreau et al. | 215/349 |
| 2003/0129738 A1* | 7/2003 | Sorenson et al. | 435/287.1 |
| 2004/0214316 A1 | 10/2004 | O'Connell | |
| 2008/0299600 A1 | 12/2008 | Bommarito | |
| 2009/0326414 A1 | 12/2009 | Peltier | |
| 2011/0087133 A1 | 4/2011 | Ching | |
| 2011/0088695 A1* | 4/2011 | DeMaria, Jr. | 128/205.13 |

FOREIGN PATENT DOCUMENTS

| | | |
|---|---|---|
| WO | 2008030820 A | 3/2008 |
| WO | 2010078482 A1 | 7/2010 |

* cited by examiner

CYTOLOGICAL CELL SAMPLE COLLECTION, STORAGE, AND TRANSPORT DEVICE

CROSS-REFERENCE TO RELATED APPLICATIONS

This application claims the benefit of and priority to U.S. Provisional Patent Application Ser. No. 61/458,407 filed Nov. 24, 2010.

FIELD OF THE INVENTION

The present invention relates generally to collection, storage, and transport of cell samples for analysis. More specifically, the present invention relates to a device for collecting, storing, and transporting anal cytological cell samples used in anal pap smear procedures.

BACKGROUND

Diagnoses indicating cancer affecting the anus have been on the rise in recent years. Awareness of this medical issue has increased in kind, with many medical professionals encouraging routine screening for early detection.

The anus is the general term for the opening at the lower end of the intestines, but can informally refer to the both anal opening and the anal canal. The anal canal spans from the rectum to the anal verge, where the canal meets the outer skin of the anus. There are a number of different cell types that make up the rectum, anal canal, and anus. The upper anal canal and some of the nearby rectal tissue comprises tiny column-like cells. Cells near the mid-section of the anal canal are cube-shaped transitional cells. Flat squamous cells comprise the lower anal canal, anal verge, and the perianal skin. Most anal cancers in the United States are squamous cell carcinomas, but anal cancer can also take the form of adenocarcinomas that develop in the cells that line the upper part of the anal canal near the rectum, or in glands located under the inner lining of the anal canal. The presence of anal cancer can show a variety of symptoms including anal bloat, lumps, rectal bleeding, itching, or discharge.

A significant number of anal cancers derive from human papillomavirus infections (HPV), a sexually transmitted disease. HPV also causes anogenital warts, which can cause anal carcinomas to form. Individuals with a history of anal warts are known to be at risk of developing anal cancer. HPV has also been shown to be a leading cause in cervical cancer in women, and, as such, methods of detection of anal cancer can be seen as counterparts to cervical methods. One such method of detecting cervical cancer is the cervical Pap smear, in which cells are collected from the cervix for analysis to detect cancerous characteristics. Currently, similar methods can be used for cells collected from the rectoanal region to detect anal cancer.

In a typical anal Pap smear procedure, a collection instrument, such as a small brush or a cotton-tipped or DACRON® swab, is inserted into the orifice. The brush or swab is swiped along the surfaces of the orifice tissue to collect a sample of the cells. These collected cells may be suspended in a liquid after collection. In either case, the cells from the collection instrument itself or from the cell suspension are examined for characteristics indicating cancerous cell growth, generally done by a trained pathologist. In some instances, mechanized examination of the cell samples has automated the initial screening to flag candidates for closer examination. The cell samples may be smeared on a glass slide or remain in suspension for the examination process. The examination process may be by use of imaging, two-sided immunoassay, or any other method of cellular sample examination.

The cell collection portion of a Pap smear procedure can be performed in a doctor's office. However, the procedure itself does not require significant invasive techniques. Thus, the need to visit a doctor specifically for such a procedure is not inherently required, so long as the collection of cells can be done in such a way that the cells are properly collected, preserved, and transported to a pathologist intact for analysis.

While devices relating to cervical Pap smears have been developed and may be applicable in spirit to the detection of anal cancer, these kits do not take into account the differences in the structural anatomy between the cervix and the anus/anal canal. One embodiment of the present invention addresses this need by a device specifically for the collection and preservation of cytological cell samples taken from the anus and anal canal.

BRIEF SUMMARY OF THE INVENTION

In certain aspects, a device for collecting, storing, and transporting cells for cytological analysis is provided. In one embodiment, the device comprises a collection assembly comprising a swab head and support shaft; a plunger connected to the support shaft opposite the swab head; a sheath having a head end and a foot end, configured to enclose at least the swab head and support shaft within its internal volume, and comprising an opening at the head end configured to pass the swab head; a base connected to the foot end of the sheath; and a containment vial; wherein the collection assembly is slidably coupled through the base at the support shaft such that at a first slide position the swab head is located within the sheath and the plunger is located external and distal to the base, and at a second slide position the swab head is displaced through the opening at the head end of the sheath; wherein the base and containment vial are configured to engage with each other to form a seal and enclose the sheath and collection assembly within an internal volume defined by the containment vial and base; and wherein the plunger comprises a lock that locks the plunger in the base when the collection assembly is in the second slide position. The lock optionally comprises a click lock that produces an audible "click" when the collection assembly is locked in the second slide position. The plunger is optionally engaged with the base when the collection assembly is in the second slide position.

In another embodiment, the device comprises a collection assembly comprising a swab head and support shaft; a plunger connected to the support shaft opposite the swab head; a sheath having a head end and a foot end, configured to enclose at least the swab head and support shaft within its internal volume, and comprising an opening at the head end configured to pass the swab head; a base connected to the foot end of the sheath; and a containment vial; wherein the collection assembly is slidably coupled through the base at the support shaft such that at a first slide position the swab head is located within the sheath and the plunger is located external and distal to the base, and at a second slide position the swab head is displaced through the opening at the head end of the sheath; wherein the base and containment vial are configured to engage with each other to form a seal and enclose the sheath and collection assembly within an internal volume defined by the containment vial and base; and wherein the plunger comprises a lock that locks the plunger in the base when the collection assembly is in the second slide position. The plunger is optionally engaged with the base when the collection assembly is in the second slide position. The lock optionally comprises a click lock that produces an audible "click" when the collection assembly is locked in the second slide position. The base optionally comprises a receiving channel to receive the plunger and engage the click lock when the collection assembly is in the second slide position. The base also optionally comprises a mating structure configured to engage with the lock.

In yet another embodiment, the device comprises a collection assembly comprising a swab head and support shaft; a plunger connected to the support shaft opposite the swab head; a sheath having a head end and a foot end, configured to enclose at least the swab head and support shaft within its internal volume, and comprising an opening at the head end configured to pass the swab head; a base connected to the foot end of the sheath; and a containment vial; wherein the collection assembly is slidably coupled through the base at the support shaft such that at a first slide position the swab head is located within the sheath and the plunger is located external and distal to the base, and at a second slide position the swab head is displaced through the opening at the head end of the sheath and the plunger is engaged with the base; wherein the containment vial is configured to engage with a cap to form a seal and enclose the sheath and collection assembly within an internal volume defined by the containment vial and cap; and wherein the plunger comprises a lock that locks the plunger in the base when the collection assembly is in the second slide position. The support shaft optionally comprises a support stop that engages with the interior surface of the head end of the sheath when the swab is in the second slide position.

Additional objects and advantages of the subject device will become apparent from the detailed description which follows.

BRIEF DESCRIPTION OF THE DRAWINGS

The above and other aspects, features and advantages of the present invention will be more apparent from the following more particular description thereof, presented in conjunction with the following drawings, wherein.

Corresponding reference characters indicate corresponding components throughout the several views of the drawings. Skilled artisans will appreciate that elements in the figures are illustrated for simplicity and clarity and have not necessarily been drawn to scale. For example, the dimensions, sizing, and/or relative placement of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will also be understood that the terms and expressions used herein have the ordinary meaning as is usually accorded to such terms and expressions by those skilled in the corresponding respective areas of inquiry and study except where other specific meanings have otherwise been set forth herein.

DETAILED DESCRIPTION

The following description is not to be taken in a limiting sense, but is made merely for the purpose of describing the general principles of the invention. The scope of the invention should be determined with reference to the claims. The present embodiments address the problems described in the background while also addressing other additional problems as will be seen from the following detailed description. Numerous specific details are set forth to provide a full understanding of various aspects of the subject disclosure. It will be apparent, however, to one ordinarily skilled in the art that various aspects of the subject disclosure may be practiced without some of these specific details. In other instances, well-known structures and techniques have not been shown in detail to avoid unnecessarily obscuring the subject disclosure.

Figure 1:
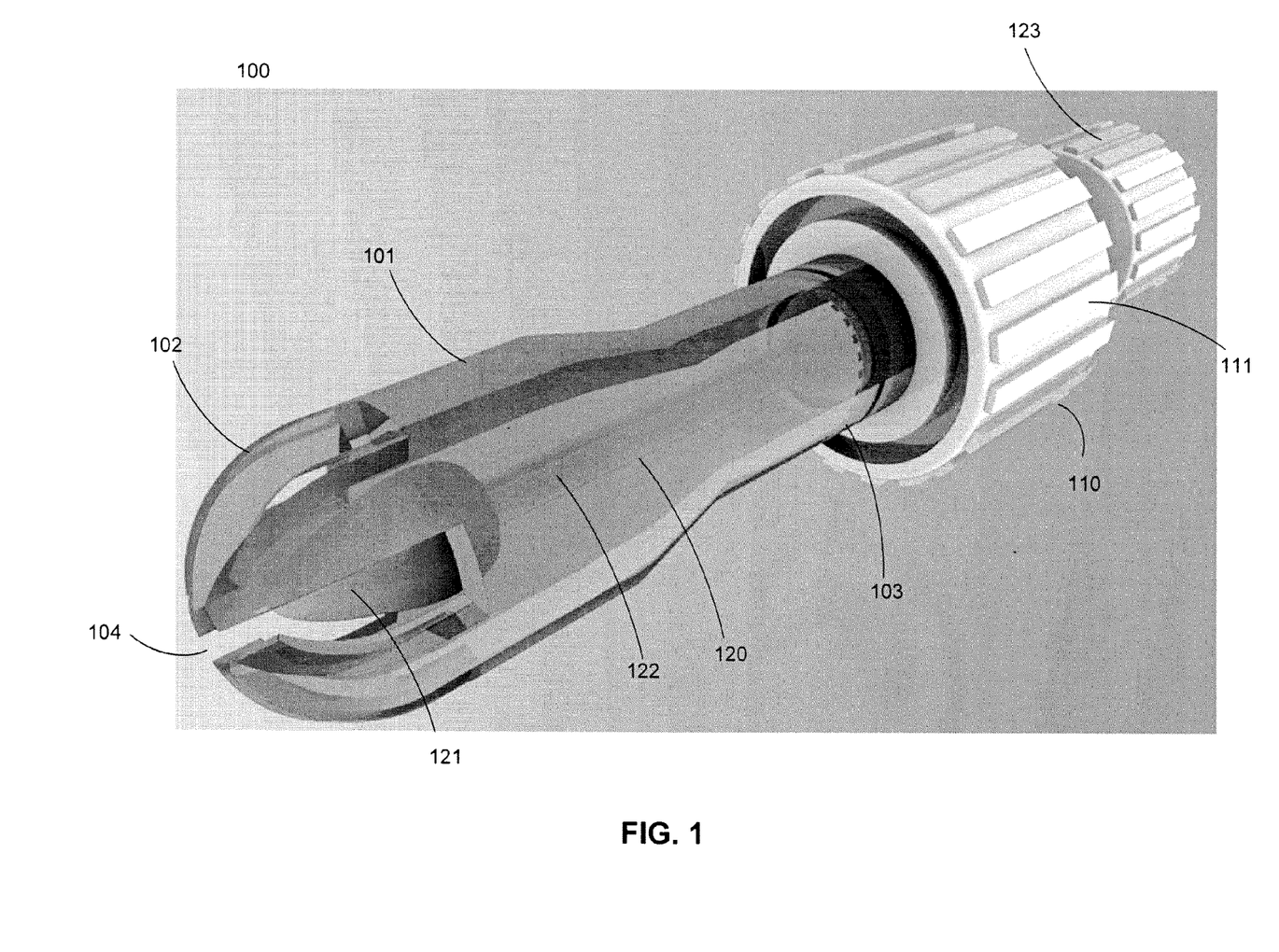
FIG. 1 is a diagram of a component of a cell collection, storage, and transport device in a first slide position according to one embodiment.

FIG. 1 shows an example embodiment of a component 100 of a device for cell collection, storage, and transport. The device in this example comprises sheath 101 having a head end 102 and foot end 103, is connected to a base 110 at the foot end 103. The device also comprises a collection assembly 120, which further comprises a swab head 121 and a support shaft 122. A plunger 123 is connected to the support shaft opposite the swab head and is located exterior of the base 110. An opening 104 on the head end 102 is configured to pass the swab head 121. The collection assembly 120 is slidably coupled through the base 110 and at the support shaft 122, allowing the collection assembly 120 to be placed at a first or second slide position. As illustrated in FIG. 1, the device is shown with the collection assembly 120 in the first slide position, wherein the swab head 121 is located within the sheath 101, and the plunger 123 is located some distance distal and external to the base 110.

The swab head, which is the collection surface of the device, can be formed of any variety of materials that effectuate proper cell collection. Examples of such materials include, without limitation, cotton, Dacron®, foam fiber, brush fibers, and flocked fibers. The swab head shape may also be formed into suitable shapes based on the anatomy of the tissues targeted for collection. Examples of such shapes include, without limitation, bulbous, triangular, conical, brush, and cylindrical.

In the example embodiment of FIG. 1, the head end 102 of the sheath is bulbous, with the opening 104 comprising a 4-petal structure. The bulbous head in this embodiment provides comfort to users of the device during the initial insertion of the device into the body cavity. Gentle pressure of the bulbous head end 102 against the entrance of the user's body cavity aids in comfortably widening the entrance to the cavity, thus allowing for proper extension of the collection assembly 120 into the interior of the body cavity for effective cell collection. The shape of the head end 102 and opening 104 can take other forms based on the body cavity or anatomy targeted for cell collection.

The lateral surface of the base 110 in FIG. 1 is illustrated with ribs 111, which aid users of the device in gripping the base during rotation of the device in the cell collection procedure. The base 110 may optionally be textured, formed in a specific shape, or comprise a grip-enhancing material to provide a user with adequate control during the cell collection procedure.

Figure 2:
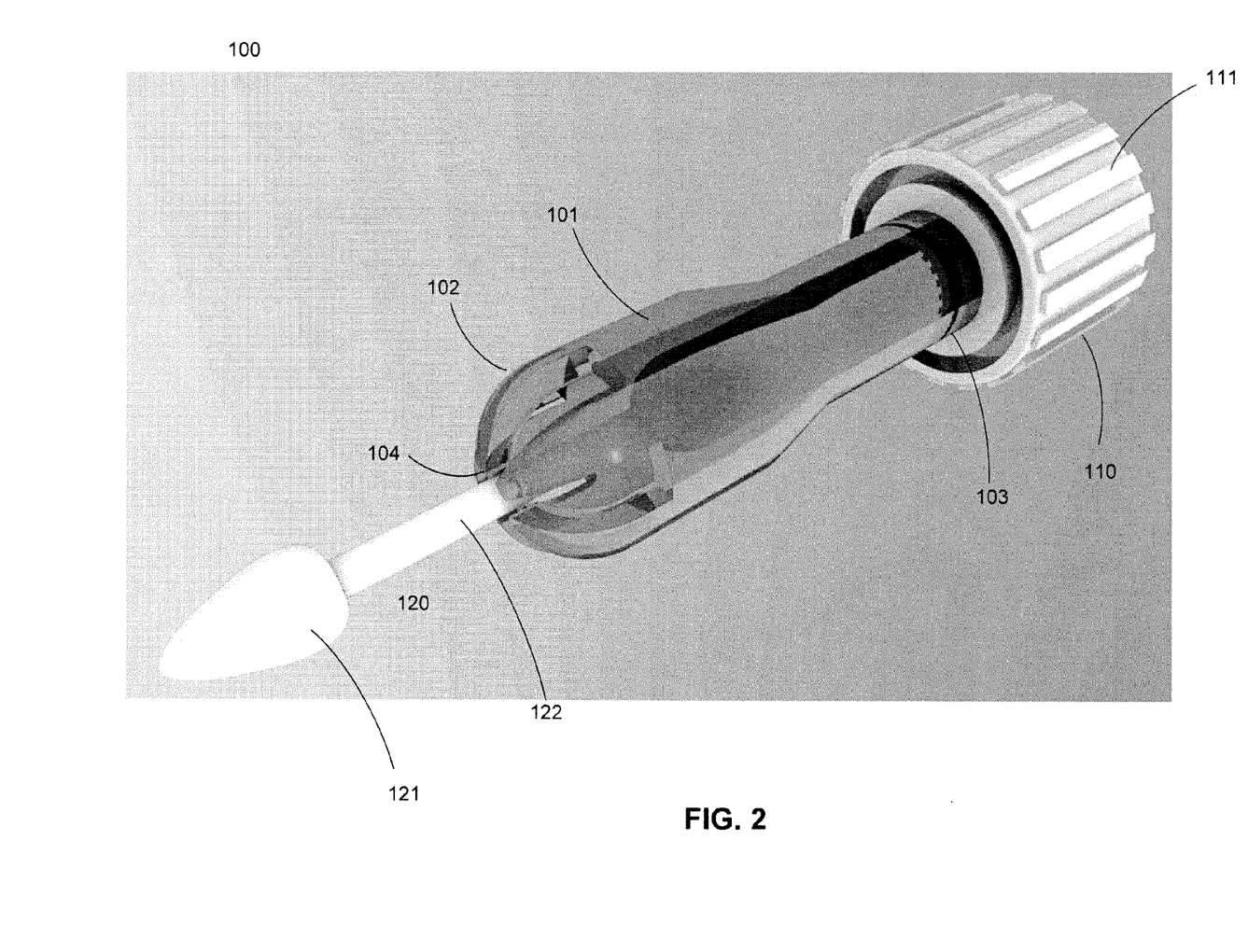
FIG. 2 is a diagram of a component of a collection, storage, and transport device in a second slide position according to one embodiment.

FIG. 2 shows the component 100 of FIG. 1 in the second slide position. When the collection assembly 120 is in the first slide position of FIG. 1, a user of the device that wishes to collect a cell sample slides the collection assembly 120 into the second slide position by pushing the plunger 123 toward the base 110. The sliding of the collection assembly 120 into the second slide position displaces the swab head 121 though the opening 104 for exposure to tissues targeted for cell collection. As can be seen in FIG. 2, when plunger 123 is pushed, the swab head 121 is extended at the exterior of the sheath 101 and is exposed for cell collection when the device is in the second slide position.

Figure 3A:
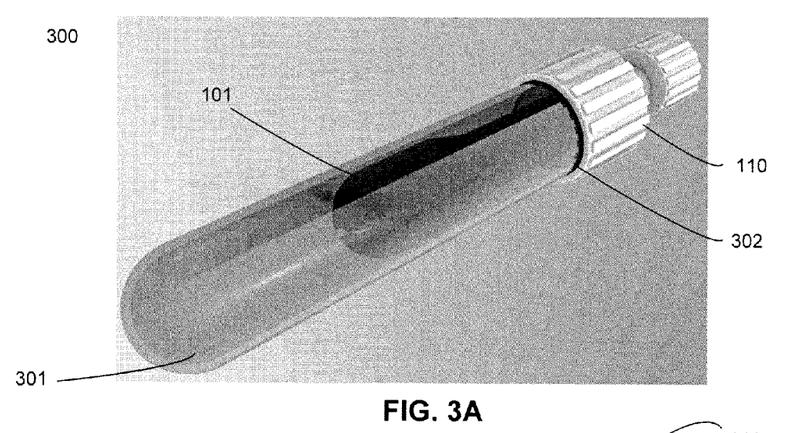
FIGS. 3a and 3b are diagrams of a cell collection, storage, and transport device in a first and second slide position, respectively, according to one embodiment.

FIG. 3a shows an example embodiment of a device 300 for cell collection, storage, and transport. This example incorporates the component 100 of FIG. 1 (i.e., the component 100 of the device in the first slide position) enclosed by a containment vial 301. The containment vial 301 is configured to engage with and form a seal 302 with base 110 to sealably enclose the sheath 101 and collection assembly. As can be seen, the sheath 101 and the collection assembly in the first slide position is enclosed within the volume defined by the containment vial 301 and base 110. Receiving the device in this configuration as part of an at-home kit, for example, would indicate to potential users that the device is in a "ready to use" state.

Figure 3B:
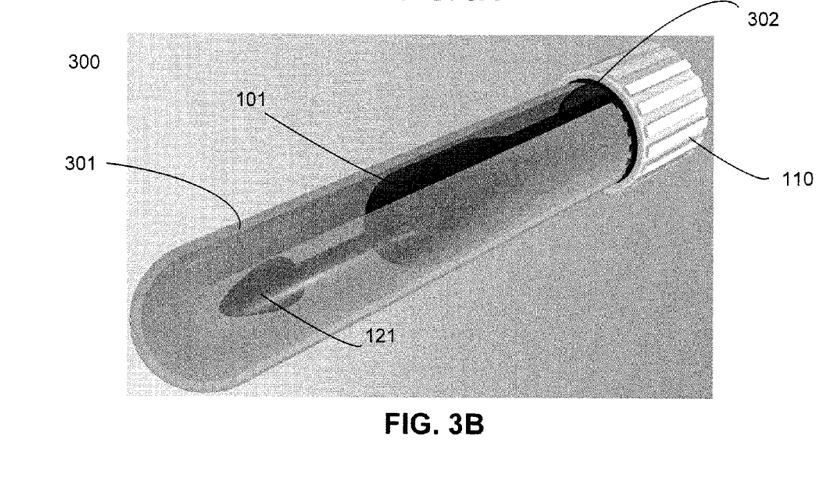

FIG. 3b shows an example embodiment of a device 300 for cell collection, storage, and transport incorporating the component 100 of FIG. 2 (i.e., the component 100 of the device in the second slide position) also enclosed by the containment vial 301. As can be seen, the swab head 121 has been passed through the opening and is located external to the sheath 101 in the second slide position. The sheath 101 and collection assembly 120 are enclosed within the internal volume defined by the containment vial 301 and base 110. The device in the second slide position can indicate to potential users that the device has been used and is ready for transport to a testing facility. FIGS. 3a and 3b illustrate that the containment vial 301 is dimensioned such that the containment vial 301 and base 110 enclose the collection assembly 120 and sheath 101 within the internal volume defined by the containment vial 301 and base 110 when the collection assembly 120 is in either the first slide position or the second slide position configurations.

The containment vial 301 can be configured to engage with the base 110 in a number of ways that provide a seal. Examples of such configurations include, without limitation, mating screw threads, pressure-fit locking threads or tabs, or other mechanisms. Sealing grommets, rings, or linings can be used to enhance the sealing capabilities of the interface between the containment vial 301 and base 110.

Locking mechanisms can be provided on plunger 123 to releasably lock the plunger 123 in place within base 110 such as for transport or storage. Although specific locking mechanisms are not illustrated, one of ordinary skill in the art after reading this description will understand that any of a number of different locking mechanisms can be used to secure plunger 123 in base 110 such as, for example, threads, tabs, friction fit and so on.

Figure 4A:
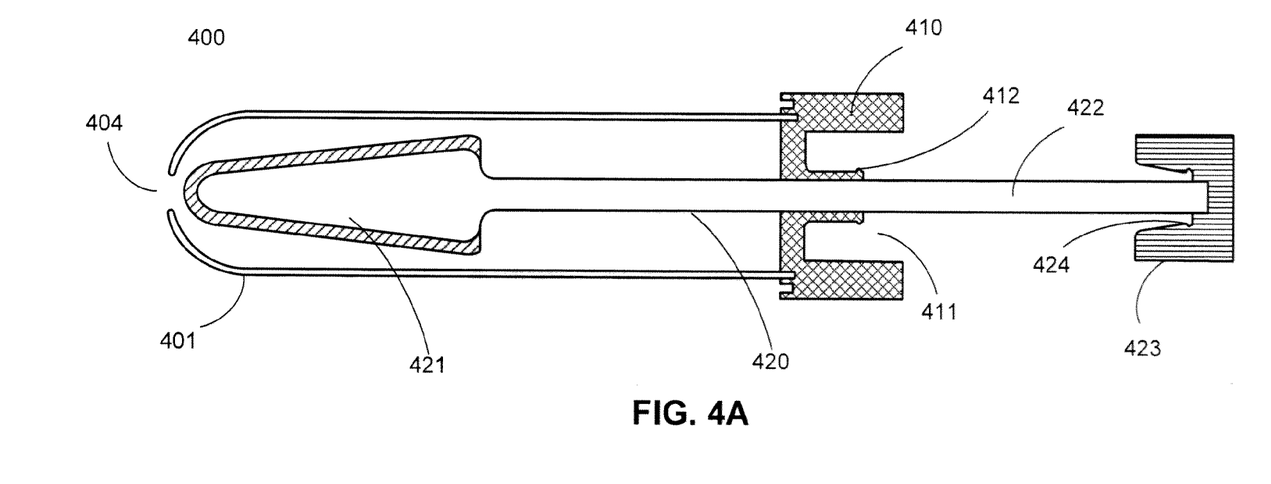
FIGS. 4a and 4b are diagrams showing the cross section of a component of a cell collection, storage, and transport device in a first and second slide position, respectively, according to one embodiment.
Figure 4B:
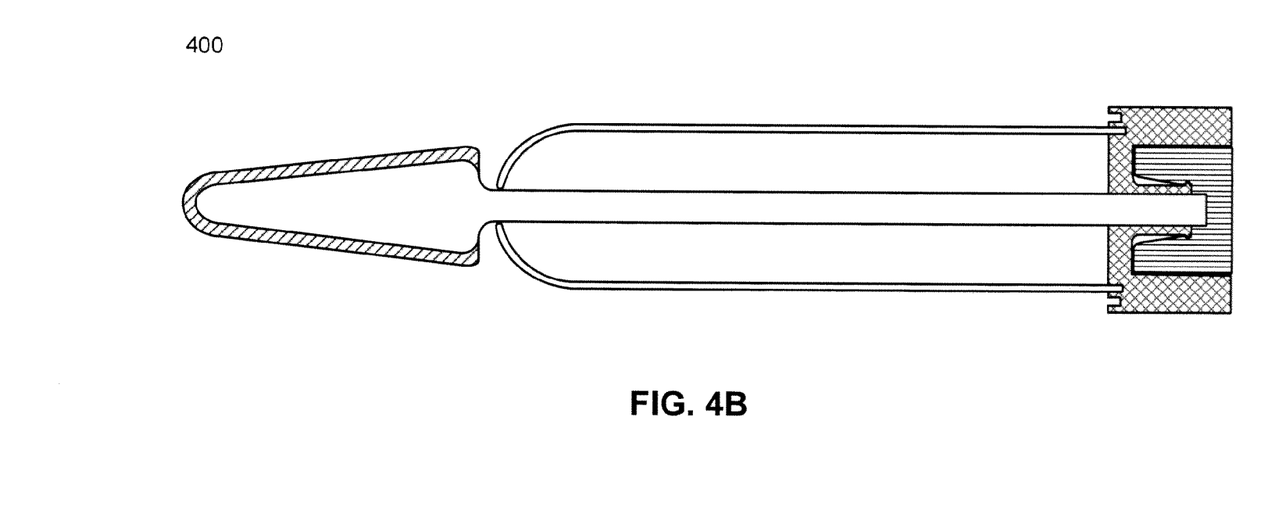

FIGS. 4a and 4b show a cross-sectional view of a component 400 of another embodiment of a device for cell collection, storage, and transport. A collection assembly 420, comprising a swab head 421 and support shaft 422, is located within a sheath 401 and is slidably coupled through a base 410. The collection assembly as shown in FIG. 4a is in a first slide position, and the plunger 423 is external and distal to the base 410. A user of the device slides the plunger 423 toward the base 410 to put the collection assembly into the second slide position, thereby extending the swab head 421 through the opening 404. The base 410 is configured to receive the plunger 423 when in the second slide position via a receiving channel 411. The plunger 423 comprises a lock 424 that engages with the base 410 while in the receiving channel 411. The lock 424 restricts the user from retracting the collection assembly 420 back into the sheath 401 (i.e., return the collection assembly 420 to the first slide position). Other benefits to the locking facility of the lock 424 include assuring to the user that the collection assembly 420 is firmly seated in the base to allow for effective collection of cells from the target tissue, providing resistance to opposing pressure during sampling, and preventing overextension of the collection assembly 420 into the user's body cavity. Incomplete extension and premature or unintended retraction of the collection assembly 420 into the sheath 401 can lead to inconsistent or faulty cell collections which would adversely affect proper cell analysis. Additionally, potential users can avoid devices found locked in the second slide position, which may indicate that the device had already been used.

The lock 424 optionally comprises a click lock, preferably configured to provide an audible "click" sound when engaged with the base 410, which signifies to the user that the collection assembly is fully extended and ready for proper cell collection. In the example embodiment of FIGS. 4a and 4b, the lock 424 is formed by a raised lip on the plunger 423, which is dimensioned for a pressure-fit with a mating structure 412 in the receiving channel 411 on the base 410. The audible click is generated as the raised lip passes into the receiving channel 411 and over the mating structure 412 on base 410.

The lock is not limited to location with respect to the base and the sheath, as the lock may optionally be located within the sheath when the collection assembly is in the second slide position. Further, the lock may optionally engage the sheath to provide the locking functionality.

As can be seen in FIG. 4b, the plunger is formed to be flush with the shape of the receiving channel and with the outer surface of the base when in the second slide position. In one embodiment, the device comprises a circular base that is configured with a circular receiving channel at a specified depth. The plunger is configured with a complementary circular form that sits flush with the sides of the receiving channel when the collection assembly is in the second slide position, and with a specified thickness matching that of the depth of receiving channel such that the plunger is also flush with the outer surface of the base.

The plunger 423 can also be formed into any number of shapes based on the intended methods for collecting or the anatomy of the tissues targeted for cell collection. For example, a ball-type plunger may be contemplated to aid in the rotation of the device during the collection stage.

The receiving channel 411 and lock 424 may be configured to be sealably engaged to resist leakage of fluid, if suitable collection and storage fluid is used. Mechanisms to form such seals while retaining the "click" functionality include mating screw threads on both the plunger 423 or base 410, or locking tabs, and may be combined with sealing grommets or linings to enhance the fluid seal.

In the embodiment illustrated in both FIGS. 4a and 4b, the containment vial (not shown) engages with and forms a seal with the base 410 to enclose the sheath 401 and collection assembly 420 when the collection assembly 420 is in either the first slide position or the second slide position.

In an example of using the device in an at-home anal cytological cell collection procedure, a user receives the device with the sheath and collection assembly enclosed the containment vial, with the collection assembly in the first slide position. The user first removes the containment vial to expose the sheath. The opening on the sheath is pressed against the anal entrance. Pressing the bulbous head end of the sheath against the anal entrance provides greater comfort to the user in guiding the swab head into the anal canal, as the insertion of the sheath helps to widen the anal entrance and resists the outward pressure from the muscles in the external anal sphincter. The plunger is then displaced to move the collection assembly from the first slide position into the second slide position and locked via the click lock into the second slide position. The user, hearing the click of the click lock, is then assured that the swab head is properly extended and exposed to the rectal tissue for collection. With the device still firmly inserted and in the second slide position, the user rotates the device to effectuate cell collection. To ensure proper collection, the user optionally rotates the device both clockwise and counterclockwise multiple times. In a non-limiting example, the user may optionally rotate the device five times clockwise and five times counterclockwise. Afterwards, the user gently removes the device from the anus, places the containment vial over the sheath and collection assembly and engages the collection vial with the base to seal it. The entire device can then be transported to a facility for analysis.

According to aspects within the present disclosure, the device can be used for dry collection of cells at targeted tissues. However, wet collection and containment may also be implemented using the device. For instance, the swab head may be pre-moistened with a suitable cell collection fluid, or the containment vial may be pre-filled with fluid suitable to suspend or store collected cells for transport. Additionally, suitable collection, suspension, or storage fluid may be provided for the user to apply.

Figure 5:
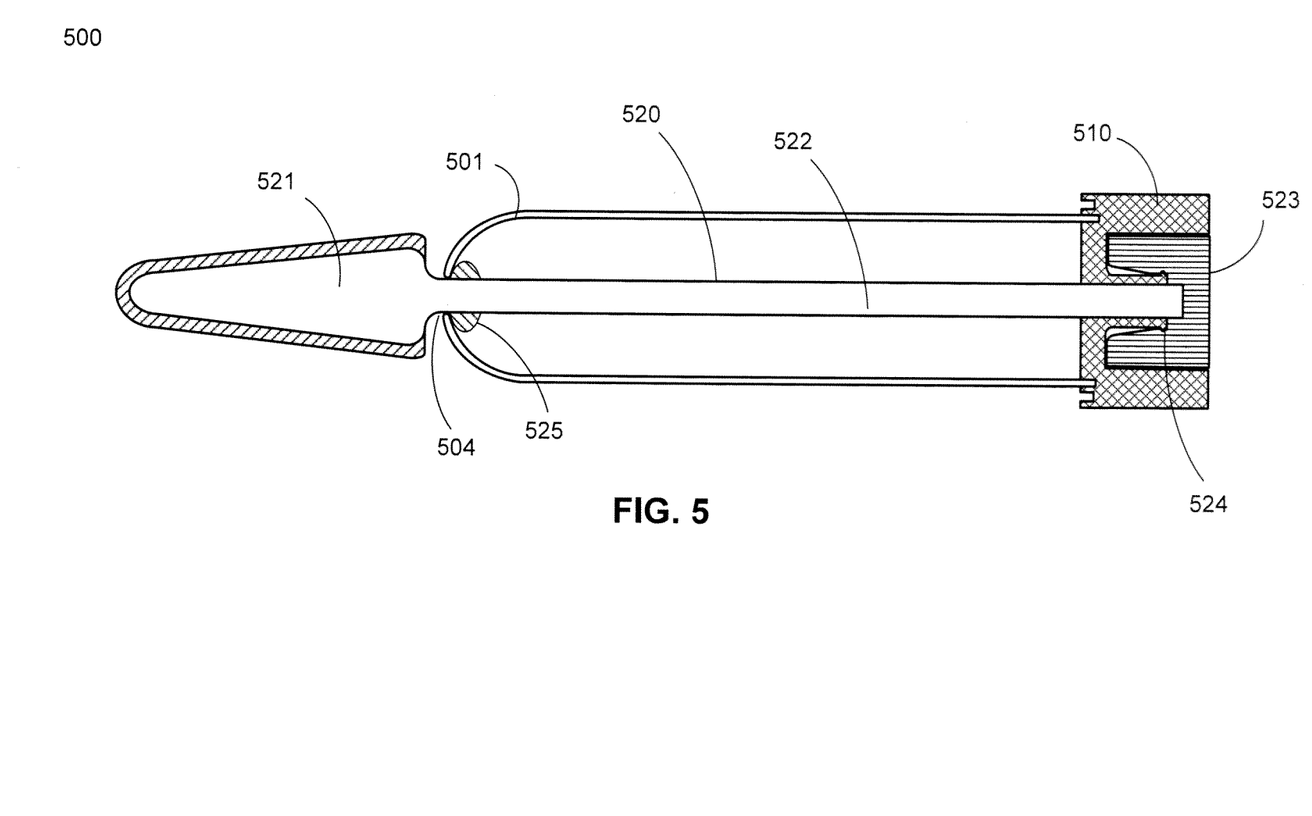
FIG. 5 is a diagram showing the cross section of a component of a cell collection, storage, and transport device in a second slide position, respectively, according to one embodiment.

FIG. 5 illustrates another embodiment of a component 500 of a device for cell collection, storage, and transport according to aspects of the present disclosure. The component 500 comprises a collection assembly 520 comprising a swab head 521 and support shaft 522; a plunger 523 connected to the support shaft 522 opposite the swab head; a sheath 501 having a head end and a foot end, configured to enclose at least the swab head 521 and support shaft 522 within its internal volume, and comprising an opening 504 at the head end configured to pass the swab head 521; a base 510 connected to the foot end of the sheath 501; and a containment vial (not shown); wherein the collection assembly 520 is slidably coupled through the base 510 at the support shaft such that at a first slide position the swab 521 head is located within the sheath 501 and the plunger 523 is located external and distal to the base 510, and at a second slide position the swab head 521 is displaced through the opening 504 at the head end of the sheath 501 and the plunger 523 is engaged with the base 510; wherein the base 510 and containment vial (not shown) are configured to engage with each other to form a seal and enclose the sheath 501 and collection assembly 520 within an internal volume defined by the containment vial (not shown) and base 510; and wherein the plunger 523 comprises a lock 524 that locks the plunger 523 in the base 510 when the collection assembly 520 is in the second slide position. The component 500 in FIG. 5 is shown in the second slide position. The support shaft 522 optionally comprises a support stop 525 that engages with the interior surface of the head end of the sheath 501 when the swab 521 is in the second slide position.

The device, while applicable to at-home cell collection procedures, may be used by medical professionals in hospitals and clinics as it offers a convenient configuration for cell collection, containment, and transport.

The description of the invention is provided to enable any person skilled in the art to practice the various embodiments described herein. While the present invention has been particularly described with reference to the various figures and embodiments, it should be understood that these are for illustration purposes only and should not be taken as limiting the scope of the invention.

There may be many other ways to implement the invention. Various functions and elements described herein may be partitioned differently from those shown without departing from the spirit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments of the invention described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

I claim:

1. A cytological device, comprising:
    a collection assembly, comprising a swab head and a support shaft,
    a plunger connected to the support shaft opposite the swab head,
    a sheath having a head end and a foot end, configured to enclose at least the swab head and support shaft within its internal volume, and comprising an opening at the head end configured to pass the swab head;
    a base connected to the foot end of the sheath; and
    a containment vial;
    wherein the collection assembly is slidably coupled through the base at the support shaft such that at a first slide position the swab head is located within the sheath and the plunger is located external and distal to the base, and at a second slide position the swab head is displaced through the opening at the head end of the sheath and the plunger form fits onto the base;
    wherein the plunger comprises a lock located on a radially outward facing surface of the plunger and is shaped to snap fit into a radially inward facing surface of the base when the collection assembly is in the second slide position; and
    the base and containment vial are configured to engage with each other to form a seal and enclose the sheath and collection assembly within an internal volume defined by the containment vial and base.

2. The device as in claim 1 wherein the base comprises a receiving channel to receive the plunger and engage the lock when the collection assembly is in the second slide position and wherein the receiving channel and the base are complimentary geometric structures.

3. The device as in claim 2 wherein the base further comprises a mating structure configured to engage with the lock.

4. The device as in claim 1 wherein the support shaft comprises a support stop;
  wherein the support stop is distal of the swab head and protrudes radially outward from the support shaft; and
  wherein the head end of the sheath curves radially inward towards the support shaft, such that the radius of the support stop is larger than the opening at the head end of the sheath, and the support stop comes into contact engages with the interior surface of the head end of the sheath when the swab is in the second slide position.

5. The device as in claim 1 wherein the lock comprises a click lock configured to produce an audible click when the collection assembly is locked in the second slide position.

6. The device as in claim 1 wherein the swab head is pre-moistened with a cell sample collection fluid.

7. The device in claim 1 wherein the containment vial is pre-filled with a cell suspension fluid.

8. The device in claim 1 wherein a radially outward surface of the plunger sealably couples to a radially inward surface of the base when the swab is in the second slide position.

9. A cytological device, comprising:
  a collection assembly, comprising a swab head and a support shaft,
  a plunger connected to the support shaft opposite the swab head,
  a sheath having a head end and a foot end, configured to enclose at least the swab head and support shaft within its internal volume, and comprising an opening at the head end configured to pass the swab head; and
  a base connected to the foot end of the sheath;
  wherein the collection assembly is slidably coupled through the base at the support shaft such that at a first slide position the swab head is located within the sheath and the plunger is located external and distal to the base, and at a second slide position the swab head is displaced through the opening at the head end of the sheath and the plunger form fits on to the base;
  wherein the plunger comprises a lock located on a radially outward facing surface of the plunger and is shaped to snap fit into a radially inward facing surface of the base when the collection assembly is in the second slide position.

10. The device in claim 9 further comprising a containment vial.

11. The device in claim 10 wherein the base and the containment vial are configured to engage with each other to form a seal and enclose the sheath and collection assembly within an internal volume defined by the containment vial and base.

12. The device as in claim 9 wherein the base comprises a receiving channel to receive the plunger and engage the lock when the collection assembly is in the second slide position and wherein the receiving channel and the base are complimentary geometric structures.

13. The device as in claim 12 wherein the base further comprises a mating structure configured to engage with the lock.

14. The device as in claim 9 wherein the lock comprises a click lock configured to produce an audible click when the collection assembly is locked in the second slide position.

15. The device as in claim 9 wherein the support shaft comprises a support stop;
  wherein the support stop is distal of the swab head and protrudes radially outward from the support shaft; and
  wherein the head end of the sheath curves radially inward towards the support shaft, such that the radius of the support stop is larger than the opening at the head end of the sheath, and the support stop comes into contact with the interior surface of the head end of the sheath when the swab is in the second slide position.

16. The device as in claim 9 wherein the swab head is pre-moistened with a cell sample collection fluid.

17. The device as in claim 9 wherein the base comprises a grip-enhancing structure.

18. The device in claim 9 wherein the containment vial is pre-filled with a cell suspension fluid.

19. The device of claim 9 wherein a radially outward surface of the plunger sealably couples to a radially inward surface of the base when the swab is in the second slide position.

20. The device in claim 9 wherein the swab head comprises flocked fibers.

* * * * *